United States Patent [19]

Jones et al.

[11] 4,196,277

[45] Apr. 1, 1980

[54] PERFLUOROISOPROPYLIDENE DIANHYDRIDE AND POLYIMIDES PREPARED THEREFROM

[75] Inventors: Robert J. Jones, Hermosa Beach; Michael K. O'Rell, Manhattan Beach, both of Calif.

[73] Assignee: TRW Inc., Redondo Beach, Calif.

[21] Appl. No.: 914,327

[22] Filed: Jun. 12, 1978

Related U.S. Application Data

[63] Continuation of Ser. No. 706,989, Jul. 19, 1976, abandoned.

[51] Int. Cl.² .............................................. C08G 73/10
[52] U.S. Cl. .................. 528/208; 260/345.2; 260/346.3; 528/70; 528/73; 528/74; 528/125; 528/172; 528/185
[58] Field of Search ............ 260/345.2, 346.3, 47 CP, 260/78 TF; 528/185, 208, 172, 125, 70, 73, 74

[56] References Cited

U.S. PATENT DOCUMENTS

| | | | |
|---|---|---|---|
| 3,356,648 | 12/1967 | Rogers | 260/47 |
| 3,879,428 | 4/1975 | Heath et al. | 260/346.3 |

*Primary Examiner*—Lester L. Lee
*Attorney, Agent, or Firm*—John J. Connors; Donald R. Nyhagen

[57] ABSTRACT

This invention relates to a novel aromatic dianhydride and more particularly to the use of said dianhydride for the preparation of thermally stable high-molecular weight polymers including, for example, polybenzimidazoles, polypyrrones, polyimides, and the like. This dianhydride is obtained by reacting a stoichiometric amount of a disodium salt of 2,2-bis(4-hydroxyphenyl) hexafluoropropane with 4-chloro-N-phenylphthalimide to obtain an intermediate, 2,2-bis[4-(3,4-phenylphthalimidephenoxy)phenyl] hexafluoropropane, which is oxidized to the corresponding bis[4-(3,4-dicarboxyphenoxy)phenyl]perfluoroisopropylidene dianhydride.

4 Claims, No Drawings

PERFLUOROISOPROPYLIDENE DIANHYDRIDE AND POLYIMIDES PREPARED THEREFROM

This is a continuation, of application Ser. No. 706,989, filed July 19, 1976, now abandoned.

BACKGROUND OF THE INVENTION

Polyimides, because of their outstanding thermal stability, have been favored for use in advanced engineering structures. In the past, polyimides were difficult to fabricate because of their insolubility in most of the more common solvents. The solubility problem was partially solved by using a polyamide-acid intermediate for product fabrication. During the final fabrication step, imidization of the polyamide-acid is easily accomplished to give the desired end product. While this solved the solubility problem, it did not successfully solve a void problem caused by water liberated during imidazation when the polyamide-acid was cured. The presence of voids in the final product is very undesirable because they reduce the mechanical properties of the product.

In U.S. Pat. No. 3,528,950, a solution of the void problem was offered. In this patent, a fully imidized prepolymer having reactive end groups was formed. In this way, the water of imidization was removed before final cure of the prepolymer during fabrication of the polyimide product. Although this substantially solved the void problem, solvent solubility was not as desirable as many fabricators would prefer.

Subsequently, U.S. Pat. No. 3,812,159 taught a dianhydride monomer containing a phenylphenoxy sulfone linkage which could be used in the process taught by U.S. Pat. No. 3,528,950, and which would provide a polyimide structure with improved solubility. The characteristics and synthesis methods for these polyimides are taught in U.S. Pat. No. 3,699,075.

SUMMARY OF THE INVENTION

While U.S. Pat. No. 3,812,159 solves the solubility problem, the high temperature stability of the sulfone containing polyimide is not as desirable as it could be. Thus, the present invention seeks to improve the chemical and thermal stability of polyimides by incorporating an aromatic fluorine dianhydride compound into the polymeric chain. The compound may be characterized by the following formula:

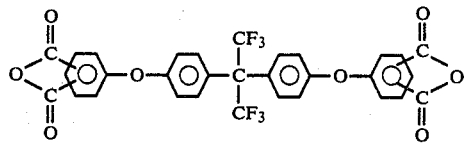

This compound is synthesized by an aromatic nucleophilic substitution of the chloro group on 4-chloro-N-phenylphthalimide with a phenoxide ion. This reaction is taught in substantial detail in Ser. No. 113,747, filed Feb. 8, 1971, now U.S. Pat. No. 3,965,125. The resultant coupling compound is then hydrolyzed to the desired dianhydride. Polyimides having hexafluoro substituents in the polymer structure can be synthesized by reacting the dianhydride with an appropriate diamine.

DESCRIPTION OF THE PREFERRED EMBODIMENTS

Preparation of a high molecular weight dianhydride having the formula:

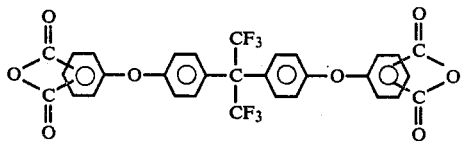

is initiated by reacting stoichiometric amounts of 2,2-bis(4-hydroxyphenyl)hexafluoropropane with sodium hydroxide to produce the disodium salt according to the following:

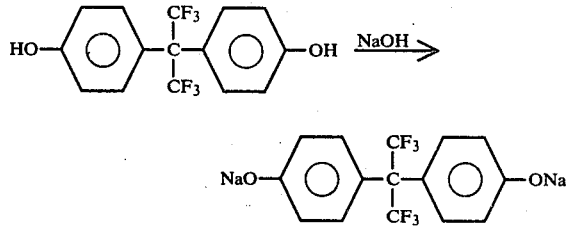

This reaction produces an intermediate compound which is sufficiently active to enter into a nucleophilic displacement reaction with the chloro-substituent on 4-chloro-N-phenylphthalimide to produce 2,2-bis[4-(3,4-phenylphthalimidephenoxy)phenyl]hexafluoropropane according to the following:

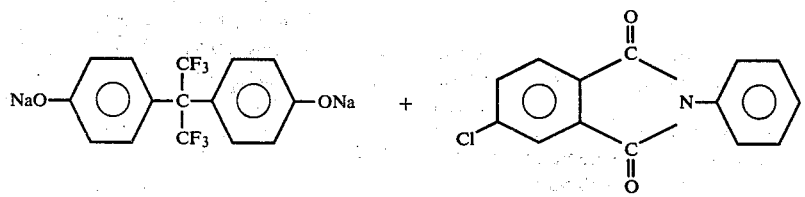

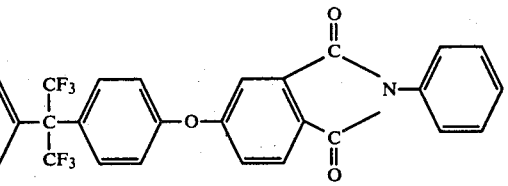

Hydrolysis and subsequent dehydration of the compound to the corresponding dianhydride is accomplished by reacting the compound in the presence of aqueous sodium hydroxide followed by acidification and dehydration.

The following example teaches the preferred method of synthesizing bis[4-(3,4-dicarboxyphenoxy)phenyl]-hexafluoropropane dianhydride.

EXAMPLE 1

Approximately 50.42 gm (0.15 mole) of 2,2-bis(4-hydroxyphenyl)hexafluoropropane was dissolved in 240 gm of dimethyl acetamide and 125 ml toluene heated to 60° C. under a nitrogen atmosphere and containing 13.20 gm (0.33 mole) sodium hydroxide and 5 ml water. The mixture was heated to reflux and the water was removed by means of a Dean-Stark trap. After all of the water was removed, the toluene was removed by distillation until the pot temperature reached 155° C.

To the disodium salt prepared above in 280 g dimethyl acetamide was added 84.98 g (0.33 mole) 4-chloro-N-phenylphthalimide. The reaction mixture was heated at 150° C. for 48hours and then poured into 2000 ml of ice water. The precipitate was collected by filtration and washed well with water. Recrystallization from 2-propanol afforded 85 g (73%) of bis[4-(3,4-phenylphthalimidephenoxy)phenyl] hexafluoropropane; mp 1975°-200° C.

ANALYSIS: Calculated for $C_{43}H_{24}N_2O_6F_6$: C, 66.27; H, 3.08; N, 3.60. Found: C, 66.29; H, 3.27; N, 3.52.

To a solution of 12 g (0.30 mole) of sodium hydroxide in 108 ml of water was added 54.25 g (0.07 mole) of the bis(imide). The mixture was refluxed for 48-hours under a nitrogen atmosphere and then the solution was diluted with 500 ml of water. The basic solution was treated with charcoal, filtered and acidified with 2 N nitric acid to pH 2. The tetraacid was collected by filtration, washed with water and dried to give 35.2 g of product; mp 145°-150° C.

The tetraacid was converted into its corresponding dianhydride by treating it with acetic anhydride. A mixture of 33.0 g (0.05 mole) of tetraacid and 200 ml of acetic anhydride was refluxed for 6-hours, then allowed to cool. The resulting precipitate was collected by filtration and air dried. Recrystallization from toluene/hexane afforded 20.3 g of colorless dianhydride; mp 228°-230° C.

ANALYSIS: Calculated for $C_{31}H_{14}O_8F_6$: C, 59.25; H, 2.25; O, 20.37; and F, 18.14. Found: C, 60.05; H, 2.65; and N, 0.06.

As suggested previously, this dianhydride or diacid can be used to produce polyimides or polyamides when reacted with a diamine. Because of the fluorine substituent on the dianhydride, the resulting polyimides or polyamides have improved chemical and thermal stability. The reaction of bis[4,-(3,4-dicarboxyphenoxy)phenyl] perfluoroisopropylidene dianhydride with a diamine will produce a polyimide which can be illustrated by the idealized formula:

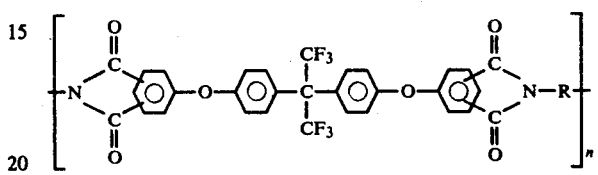

wherein n is an integer sufficient to provide a structure having an average molecular weight of at least 5000 and R is an organic radical of 5 to 22 atoms which may be an aliphatic radical, including alicyclic, or an aromatic radical having one or more benzene rings or fused polynuclear rings.

The steps for the preparation of these polyimides are known in the art. Generally, these dianhydrides are reacted by mixing them with a diamine to produce a polyamide-acid. Upon completion of the addition of a stoichiometric amount of the diamine, the resulting amide-acid is dehydrated to the corresponding imide. Further details of the imide polymerization process may be found in numerous United States patents, for example U.S. Pat. No. 3,179,634.

The polyfunctional amines which are particularly preferred are illustrated hereinbelow and include, for example:

TABLE I 2,5-dimethylhexamethylene diamine
2,5-dimethylheptamethylene diamine
5-methyl-nonamethylene diamine
2,17-diamino-eicosadecane
1,4-diamino-cyclohexane
1,10-diamino-1,10-dimethyldecane
1,12-diamino-octadecane
para-phenylene diamine
meta-phenylene diamine
4,4'-diamino-diphenyl propane
4,4'-diamino-diphenyl methane
benzidine
4,4'-diamino-diphenyl sulfide
4,4'-diamino-diphenyl sulfone
3,3'-diamino-diphenyl sulfone 4,4'-diamino-diphenyl ether
1,5-diamino-naphthalene
3,3'-dimethoxy benzidine
2,4-bis(beta-amino-t-butyl)toluene
bis(para-beta-t-butyl-phenyl)ether
bis(para-beta-amino-t-butyl-phenyl)ether
bis(para-beta-methyl-delta-amino-pentyl)benzene
bis(para-1,1-dimethyl-t-amino-pentyl)benzene
1-isopropyl-2,4-metaphenylene diamine
m-xylylene diamine
hexamethylene diamine
heptamethylene diamine octamethylene diamine
nonamethylene diamine
decamethylene diamine
diamino-propyl tetramethylene diamine
3-methylheptamethylene diamine
4,4'-dimethylheptamethylene diamine
2,11-diamino-dodecane
1,2-bis(3-amino-propoxy)ethane
2,2-di methyl propylene diamine
3-methoxy-hexamethylene diamine
3,3'-dimethyl benzidine
methylene dianiline(4,4'-diaminophenyl methane)
oxydianiline(4,4'-diaminophenyl ether)
3,3'-diamino diphenyl
1,4-diamino naphthalene
4,4'-diamino diphenyl ketone
bis(4-amino-phenyl)-d,d'-p-xylylene diamine, etc.

In addition to the aromatic diamines which may be used to prepare the polyimides, the aromatic diisocyanates may be used, and include, for example, toluene diisocyanate, either the 2,4-isomer, the 2,6-isomer or mixtures of said isomers; 4,4'-di-o-tolylene diisocyanate; 4,4'-methylene-di-o-tolylisocyanate; m-phenylene diisocyanate, 4;-methoxy-1,3-phenylene diisocyanate; 4-chloro-1,3-phenylene diisocyanate; 4,4-diisocyanate, 4,4-diisocyanatodiphenyl sulfone; 1,5-naphthalene diisocyanate; 3,3'-bitolylene-4,4'-diisocyanate, mesitylene diisocyanate; 3,3'-dimethyl-4,4'-diisocyanatodiphenyl methane; 4-isopropyl-1,3-phenylene diisocyanate; 2,4'-diisocyanatodiphenyl ether, 4,4'-diisocyanatodiphenyl ether; 3,3'-dimethyl-4,4'-diisocyanatodiphenyl methane, etc.

Perhaps as suitable as the isocyanate terminated compounds are the nitrile terminated compounds. Where increased thermo-oxidative stability is sought, a nitrile terminated perfluoroisopropylidene compound should be considered.

The following example illustrates the method employed in preparing the polyimide in accordance with this invention.

EXAMPLE II

To a stirred solution of 0.865 g (8 mmole) of m-phenylenediamine (MPD) in 15 ml of dimethylacetamide (DMAC) was slowly added portionwise 5.02 g (8 mmole) of bis[4-(3,4-dicarboxyphenoxy)phenyl]perfluoroisopropylidene dianhydride (BFDA) at such a rate that each portion of dianhydride was allowed to dissolve before the next portion was added. The reaction was run under a nitrogen blanket and was cooled with a water bath. The residual bis[4-(3,4-dicarboxyphenoxy)phenyl] perfluoroisopropylidene dianhydride (BFDA) was washed into the reaction flask with an additional 5 ml of dimethylacetamide (DMAC) to give a 23 percent by weight solids solution. The reaction mixture was stirred for three hours after the last of the BFDA had been added and then was transferred to a vacuum oven. The solvent was removed at 100° C. and the resulting amide/acid polymer was imidized by heating it to 180° C. for four hours. The tough, flexible polymer was found to have an inherent viscosity of 0.42 dl/g ($H_2SO_4$ at 30° C.).

The linear polyimide prepared from BFDA/MPD was characterized for physical properties and the results are given in Table II.

TABLE II
CHARACTERIZATION OF LINEAR POLYIMIDES

| Property | Polyimide BFDA/MPD | BSDA/MPD[c] |
|---|---|---|
| Inherent Viscosity[a] | 0.42 | 0.40 |
| Solubility, % w/w | | |
| DMF or DMAC | 15–20 (20° C.) | 15–20 (20° C.) |
| (dimethylformamide) | 25 (100° C.) | 25 (100° C.) |
| Dioxane | ca. 5 | <1 |
| Thermo-oxidative Stability | | |
| a. Initial Wt. loss in TGA, °C.[b] | 400° C. | 410° C. |
| b. Weight retention during aging at 316° C. (600° F.), % w/w | | |
| 100 hours | 97 | 92 |
| 700 hours | 91 | 80 |
| 1000 hours | 88 | 60 |

[a]$H_2SO_4$, 30° C.
[b]3° C./min., 100 ml/min. air flow.
[c]U.S. 3,699,075; bis[4-(3,4-dicarboxyphenoxy)phenyl]sulfone dianhydride (BSDA)/m-phenylene diamine (MPD)

These results are compared with the BSDA/MPD polymer in the same Table. As can be seen from the results in Table I, the polymers display similar solubility properties. The significant difference between the two polymers is in the long-term thermooxidative stability. At 600° F., the BFDA/MPD displayed superior thermo-oxidative stability over the PSDA/MPD polymer as judged by weight retention of the polymer sample during the 1000-hour aging.

These polyimide can be used as a matrix for laminated glass or graphite structures having high thermal stability, for example, ablative structures. High temperature coatings and adhesives are a few additional applications for which these polyimides are particularly suited.

It is obvious that anti-oxidants and/or stabilizers and the like may be used in combination with the polymeric materials if desired. Moreover, the polymeric materials obtained from the dianhydrides of this invention may be used in combination with various fillers and reinforcing agents including silica, glass, carbon black, metal, fibers, dye-stuffs, pigments, graphite, and various mixtures thereof.

We claim:
1. An aromatic dianhydride compound having the structure:

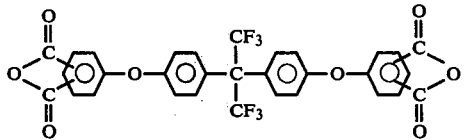

2. A polyimide consisting essentially of recurring units:

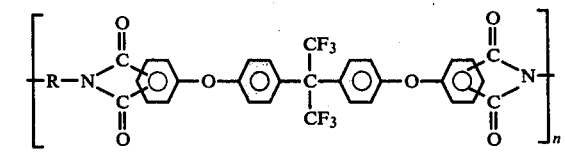

where n is an integer sufficient to provide a structure having an average molecular weight of at least 5000 wherein R is an organic radical of 5 to 22 atoms selected from the group consisting of divalent aliphatic radicals and divalent aromatic radicals.

3. The polyimide according to claim 2 further characterized in that R has at least one benzene ring.

4. The polyimide according to claim 2 further characterized in that R has an arylene radical containing two benzene rings.

* * * * *